United States Patent [19]

Gruber et al.

[11] 4,247,714
[45] Jan. 27, 1981

[54] COPOLYMERIZABLE, ULTRAVIOLET LIGHT ABSORBER 4-ACRYLOYLOXYBENZAL-1-ALKYL-1-PHENYLHYDRAZONE

[75] Inventors: Bruce A. Gruber, Worthington, Ohio; Donald H. Lorenz, Basking Ridge, N.J.

[73] Assignee: GAF Corporation, New York, N.Y.

[21] Appl. No.: 125,019

[22] Filed: Feb. 27, 1980

[51] Int. Cl.$^3$ .............................................. C07C 69/54
[52] U.S. Cl. ..................................... 560/221; 424/59; 526/312
[58] Field of Search .......................... 560/221; 424/59

[56] References Cited

U.S. PATENT DOCUMENTS

| | | | |
|---|---|---|---|
| 3,365,421 | 1/1968 | Horton et al. | 560/221 |
| 4,150,987 | 4/1979 | Anderson et al. | 260/566 B |

FOREIGN PATENT DOCUMENTS 2239634  2/1973  Fed. Rep. of Germany.

Primary Examiner—Natalie Trousof
Assistant Examiner—L. Hendriksen
Attorney, Agent, or Firm—James Magee, Jr.; Walter Katz

[57] ABSTRACT

This invention relates to copolymerizable ultraviolet light absorber compounds having the formula:

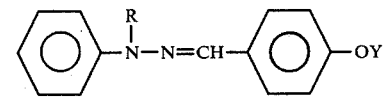

where R is hydrogen or alkyl $C_1$–$C_6$; and Y is a copolymerizable radical selected from acryloyl $C_3$–$C_{12}$, acryloyloxyalkyl $C_3$–$C_{12}$, acryloyloxyhydroxyalkyl $C_3$–$C_{12}$, and alkylacryloyloxyhydroxyalkyl $C_3$–$C_{12}$.

7 Claims, No Drawings

COPOLYMERIZABLE, ULTRAVIOLET LIGHT ABSORBER 4-ACRYLOYLOXYBENZAL-1-ALKYL-1-PHENYL-HYDRAZONE

BACKGROUND OF THE INVENTION

1. Field of the Invention

This invention relates to novel copolymerizable ultraviolet light absorber compounds, and, more particularly, to 4-acrylcyloxybenzal-1'-alkyl-1'-phenylhydrazone compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

Among the other uses of copolymerizable ultraviolet absorbers is in skin care and hair care compositions, but these generally require materials which absorb at relatively longer wavelengths then previously available.

Accordingly, it is an object of the present invention to provide novel copolymerizable ultraviolet light absorber compounds which are substantially free of the disadvantages of the prior art.

Another object of this invention is to provide novel compounds which can be copolymerized directly with monomers, such as plastic material, to provide more permanent ultraviolet light protection.

Still another object of the invention is to provide copolymerizable monomers which absorb at wavelengths suitable for skin care and hair care compositions.

These and other objects and features of the invention will be made apparent from the following more particular description of the invention.

SUMMARY OF THE INVENTION

What is provided herein are improved, novel copolymerizable ultraviolet light absorber compounds of the formula:

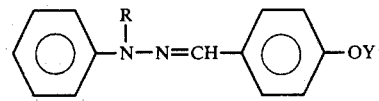

where R is hydrogen or alkyl $C_1$–$C_6$; and Y is a copolymerizable radical selected from acryloyl $C_3$–$C_{12}$, alkylacryloyl $C_3$–$C_{12}$, acryloyloxyalkyl $C_3$–$C_{12}$, and alkylacryloyloxyhydroxyalkyl $C_3$–$C_{12}$.

In the best mode of the invention, R is methyl and Y is acryloyl.

DETAILED DESCRIPTION OF THE INVENTION

The compounds of the invention contain ultraviolet light absorber and copolymerizable portions in the same molecule. These portions are effectively separated so that each can perform its own function without interference from the other. Therefore, the absorber portion does not inhibit the copolymerization, and the ethylenic radical does not affect the light absorbing properties of the molecule.

The Y radical is copolymerizable with vinyl monomers so that the ultraviolet absorber becomes an integral part of the polymer. Suitable Y groups are derived from acryloyl, alkylacryloyl, acryoyloxyalkyl, acryloyloxyhydroxyalkyl and alkylacryloyloxyhydroxyalkyl, having from $C_3$—$C_{12}$ carbon atoms. The preferred groups are acryloyl, methacryloyl, acryloyloxyhydroxypropyl, and methacryloyloxyhydroxypropyl. The best mode is represented by acryloyl.

The novel compounds of the invention may be prepared, e.g. from 4-hydroxybenzal-1'-alkyl-1'-phenylhydrazone by esterification with an acryloyl halide. The compounds herein are yellow solids which are insoluble in water. The benzal alkylphenylhydrazone chromophore of the compounds herein has an ultraviolet absorbance peak at about 340 nm, but no visible absorbance. The compounds of the invention absorb in the 330–400 nm range, which is particularly useful for skin and hair care compositions.

The flow sheets below illustrates the reaction for preparing the compounds of the invention.

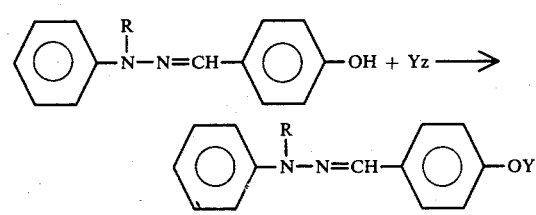

where Z is a halide and R and Y are as defined above.
Representative Y groups are

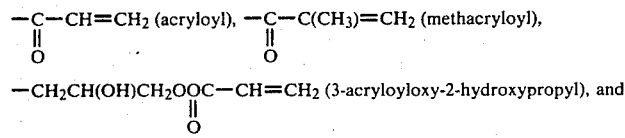

-continued

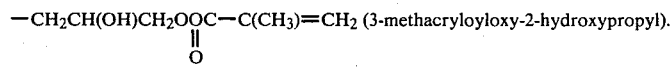
—CH₂CH(OH)CH₂OOC—C(CH₃)=CH₂ (3-methacryloyloxy-2-hydroxypropyl).
‖
O

The esterification step is carried out by reaction of the benzal alkylphenylhydrazone in a suitable solvent, such as water, with a reactive acryloyl compound, such as an acryloyl halide, e.g. acryloyl chloride or acryloyl bromide, in aqueous base, such as a sodium hydroxide solution, at room temperature. Suitably, the molar ratios of the reactants are controlled to provide at least 1:1 molar ratio of the acryloyl halide to the hydrazone starting material. The product of the reaction is precipitated, filtered and dried. The yield of the product in the esterification is about 70%.

The compounds of the invention may be copolymerized with monomers and oligomers by conventional free radical or with radiation curing, to provide useful polymeric coatings, or formulated into cosmetic preparations, such as skin and hair care products.

The following examples will describe the invention with more particularity.

EXAMPLE 1

4-Acryloyloxybenzal-1'-Methyl-1'-Phenylhydrazone

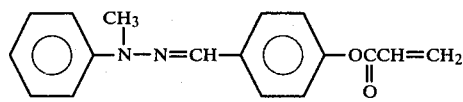

A. Hydroxybenzal-1'-Methyl-1'-Phenylhydrazone

To 50 ml of ethanol having dissolved therein 12.5 g p-hydroxybenzaldehyde (0.1 mole) is added 12.5 g (0.1 mole ) of 1-methyl-1-phenylhydrazine. The mixture is heated at reflux for 1 hour and cooled. Then water is added until the solution becomes cloudy. The solid that separates is filtered, giving 22 g (95%) of crude material. Recrystallization from methanol/water gives the product; nmr (chloroform) has singlet at δ=3.3 (3 protons) and complex multiplet centered at δ=7.2 (10 protons).

B. 4-Acryloyloxybenzal-1'-Methyl-1'-Phenylhydrazone

In 100 ml water containing 2 g NaOH is dissolved with stirring 11.3 g (0.05 mole ) 4-hydroxybenzal-1'-methyl-1'-phenylhydrazone. To the stirred solution is added dropwise 4.5 g (0.05 moles) acryloyl chloride. The solid that separates is filtered and recrystallized from ethanol/water giving 6 g (43%) product; nmr (chloroform) has singlet at δ=3.35 (3 protons), a complex multiplet centered at δ=7.3 (13 protons).

EXAMPLE 2

Copolymerization with Styrene

Into a 3-necked flask, equipped with a magnetic stirrer, thermometer heating mantle, N₂ purge apparatus and a reflux condenser is charged 50 g of styrene, 0.75 g of the UV absorber, namely, the compound of Example 1, and 69 ml of toluene. While stirring and with a nitrogen purge, the contents then are heated to 109° /c and 0.25 of benzoyl peroxide in 6 ml of toluene is added. The polymerization is continued for 17 hours. A polymer is recovered; analysis of the polymer indicates an incorporation of the UV absorber into the polymer structure.

EXAMPLE 3

4-Methacryloyloxybenzal-1'-Methyl-1'-Phenylhydrazone

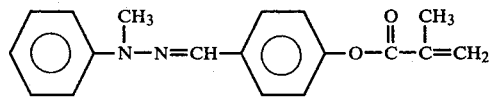

Using an equivalent amount of methacryloyl chloride in place of acryloyl chloride in Example 1, the desired methacrylate compound is obtained in comparable yield.

EXAMPLE 4

4-(3-Acryloyloxy-2-hydroxypropyloxy)benzal-1'-Methyl-1'-Phenylhydrazone

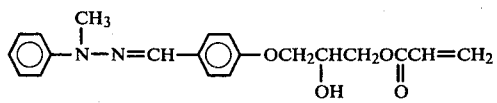

The procedure of Exammple 1 is followed except that the phenol, glycidyl acrylate and tetramethyl ammonium chloride are heated at 70°–90° C. for 5 hours, and excess glycidal acrylate removed by vacuum distillation, to provide the desired compound.

EXAMPLE 5

4-(3-Methacryloyloxy-2-hydroxypropyloxy)benzal-1'-Methyl-1'-Phenylhydrazone

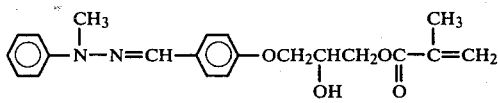

Using glycidyl methacrylate in place of glycidyl acrylate in Example 4 gives the corresponding methacrylate compound.

EXAMPLE 6

The monomer compound of Example 1 is copolymerized with another monomer by charging a flask with 150 ml ethanol, 1.5 g 4-acryloyloxybenzal-1'-methyl-1'-phenylhydrazone and 50 g vinyl pyrrolidone. The contents are heated to 75° C. under N₂ and polymerization is initiated with 0.2 g azobisisobutyronitrile (AIBN). After 1.5 hours, another 0.2 g AIBN is added and heating is continued for another 1.5 hours. The solvent is concentrated and added to stirred ether. A white precipitate of the copolymer is obtained which is filtered and dried, giving 18 g (36%) of product. A 5% aqueous solution of the copolymer is filtered; the ultraviolet spectra of the filtrate shows that the copolymer contains 5.8% of the absorber compound.

While certain preferred embodiments of the present invention have been illustrated by way of specific example it is to be understood that the present invention is in no way to be deemed as limited thereto but should be construed as broadly as all or any equivalents thereof.

What is claimed is:

1. Copolymerizable ultraviolet light absorber compounds having the formula:

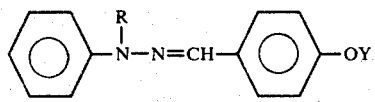

where R is hydrogen or alkyl $C_1$–$C_6$; and

Y is a copolymerizable radical selected from acryloyl $C_3$–$C_{12}$, alkylacryoyl $C_3$–$C_{12}$, and alkylacryloyloxyhydroxyalkyl $C_3$–$C_{12}$, and alkylacrylxoylohydroxyalkyl $C_3$–$C_{12}$.

2. Compounds according to claim 1 wherein R is methyl.

3. Compounds according to claim 1 in which Y is acryloyl, methacryloyl, 3-acryloyloxy-2-hydroxypropyl or 3-methacryloyloxy-2-hydroxypropyl.

4. A compound according to claim 1 which is 4-acryloyloxybenzal-1'-methyl-1'-phenylhydrazone.

5. A compound according to claim 1 which is 4-methacryloyloxybenzal-1'-methyl-1'-phenylhydrazone.

6. A compound according to claim 1 which is 4-(3-acryloyloxy-2-hydroxypropyloxy)benzal-1'-methyl-1'-phenylhydrazone.

7. A compound according to claim 1 which is 4-(3-methacryloyloxy-2-hydroxypropyloxy)benzal-1'methyl-1'-phenylhydrazone.

* * * * *